(12) United States Patent
Rise

(10) Patent No.: US 6,337,997 B1
(45) Date of Patent: Jan. 8, 2002

(54) IMPLANTABLE SEIZURE WARNING SYSTEM

(75) Inventor: Mark T. Rise, Monticello, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/459,184

(22) Filed: Dec. 10, 1999

Related U.S. Application Data

(63) Continuation of application No. 09/069,917, filed on Apr. 30, 1998, now Pat. No. 6,018,682.

(51) Int. Cl.[7] .................................................. A61N 1/36
(52) U.S. Cl. ............................................. 607/45; 607/3
(58) Field of Search ......................................... 607/45, 3

(56) References Cited

U.S. PATENT DOCUMENTS 5,311,876 A * 5/1994 Olsen et al. .................. 128/731
5,978,702 A * 11/1999 Ward et al. ...................... 607/3
6,016,449 A * 1/2000 Fischell et al. ................ 607/45

* cited by examiner

Primary Examiner—Carl Layno
(74) Attorney, Agent, or Firm—Banner & Witcoff, Ltd.

(57) ABSTRACT

Techniques for warning a patient of a possible onset of a seizure using a sensor, a signal generator and at least one implantable electrode. The electrodes are positioned to stimulate the spinal cord or under the skin. The sensor senses a parameter of the body indicative of the possible onset of a seizure. The sensor generates a sensing signal which is processed and an algorithm is utilized to determine whether the sensing signal shows a pattern indicative of a possible seizure onset. If such a pattern is recognized, the signal generator provides electrical stimulation via electrodes to generate a sensory stimulus to the body. The stimulation may provide visual, aural or touch stimulus to the patient. The patient is thereby alerted to the possibility of a seizure onset and may take appropriate action

56 Claims, 4 Drawing Sheets

IMPLANTABLE SEIZURE WARNING SYSTEM

This is a continuation of application Ser. No. 09/069,917 now U.S. Pat. No. 6,018,682, filed Apr. 30, 1998, for which priority is claimed, this parent application is incorporated herein by reference in its entirety.

BACKGROUND OF THE INVENTION

1. Field of the Invention

This invention relates to the treatment of seizure disorders and, and more particularly relates to techniques for warning patients of an epileptic seizure.

2. Description of Related Art

Epilepsy is a condition characterized by recurrent seizures which are the outward manifestation of excessive and/or hyper-synchronous abnormal electrical activity of neurons in the cerebral cortex of the brain. A seizure often occurs when the electrical activity of the brain becomes more "synchronized" as would be the case when the person is in a drowsy state.

A seizure patient may suffer from any combination of different types of seizures. Grand mal seizures are the most common form of epilepsy and are characterized by convulsions with tonic-clonic contractions of the muscles. Absence seizures (previously referred to as "petit mal") are characterized by a brief and sudden loss of consciousness. The psychomotor form of seizures is characterized by a clouding of consciousness for one or two minutes. A complex partial seizure is characterized by a complete loss of consciousness. The type of seizure experienced is typically dependent upon the function of the portion of the cerebral cortex where hypersynchronous activity is occurring. Many types of seizures generally involve the entire brain, while certain types, such as partial seizures, begin in one part of the brain and may remain local.

Regardless of the type of epilepsy, seizures significantly limit the autonomy of the patient. When hit with a seizure attack, the patient typically loses some level of control of his/her body. In most cases, seizures occur without prior warning to the patient. As a result, epileptic seizures pose a serious safety hazard to the patient as others surrounding the patient. For example, a patient hit with a sudden seizure attack while he/she is driving a car may endanger his/her own safety as well as the safety of others. Seizure patients are also exposed to a risk of bodily harm when operating machinery and even in daily activities such as crossing a street or going down stairs.

Researchers have developed a number of techniques for treating seizure disorders and its symptoms. For example, research has shown that inhibiting (namely, reducing the excitation of neurons) the substantia nigra in the brain increases the threshold for seizure occurrence. Researchers have also found that increasing the activity of neurons in the external Globus Pallidum (GPe) increases inhibition of neurons in the subthalamic nucleus which in turn inhibits neural activity in the substantia nigra. Neurosurgeons have also been able to diminish the symptoms of many neural disorders by lesioning certain brain areas, examples being lesioning the ventral portion of the internal Globus Pallidus and the Vim Thalamus for treating movement disorders. Alternatively, it has been demonstrated that open-loop Deep Brain Stimulation (DBS) at high frequencies (100 Hz or higher) of certain brain structures can alleviate, diminish, or completely stop symptoms of tremor, rigidity, akinesia or hemiballism much like creating a lesion. Electrical stimulation of the nervous system has also been used to suppress seizures. Finally, infusion of certain drugs into a region of the brain can affect the excitability of the neurons at the site of infusion as disclosed in U.S. Pat. No. 5,713,923 (Rise et al.) assigned to Medtronic, Inc.

Others have studied the effects of electrically stimulating the vagus nerve as a means of "desynchronizing" the electrical activity of the brain. It has been observed that stimulation of the vagus nerve with certain parameters caused de-synchronization of the brain's electrical activity in animal models. These concepts were disclosed by Zabara in U.S. Pat. Nos. 4,867,164 and 5,025,807. De-synchronization can be thought of as "alerting" phenomena since it reflects active mental activity.

Under another approach, researchers have devised algorithms to detect the onset of a seizure. Qu and Gotman reported a system that recognizes patterns of electrical activity similar to a template developed from recording an actual seizure. See H. Qu and J. Gotman, "A Seizure Warning System for Long-term Epilepsy Monitoring", Neurology, 1995;45:2250–2254. Similarly, Osario et. al. have reported an algorithm applied to signals recorded from intracranial electrodes capable of 100% seizure detection rate with 0% false negatives and minimal false positives. See I. Osario, M. Frei D. Lerner, S. Wilkinson, "A Method for Accurate Automated Real-time Seizure Detection", Epilepsia, Vol. 36, Suppl. 4, 1995. In each of these techniques for recognizing the onset of a seizure, the developers employ two processes. The first process is to extract certain features from the signals representing the electrical activity of the brain. Examples of the signal features include the signal power or the frequency spectrum of the signals. The second process is to recognize a pattern or set of values for those features which characterize a brain state that will reliably lead to a seizure.

Using these pattern recognition techniques, researchers have developed warning systems to alert the seizure patient of a possible seizure onset. For example, U.S. Pat. Nos. 3,863.625 and 4,566,464 disclose epileptic seizure warning systems producing audio and visual warning signals to the patient prior to the possible onset of a seizure. The warning devices are external devices which can be worn in a shirt pocket of a seizure patient. Such an approach is generally simpler in design than the above-described techniques for treatment of seizures and provides the patient prior warning of a possible seizure onset. Advantageously over the above-mentioned methods, these device allows the patient to take appropriate action to minimize physical injury to the patient and others. This approach, however, requires the patient to constantly carry around the monitoring device causing inconvenience to the patient especially if the monitoring device is misplaced. The use of audio and visual signals as the warning mechanism may also not be as effective if the device is buried underneath a heavy coat or is outside of the hearing range of the patient. In addition, this device is ineffective for seizure patients who have impaired vision or hearing.

The present invention is directed to overcoming the disadvantages of the foregoing systems.

SUMMARY OF THE INVENTION

As explained in more detail below, the present invention overcomes the above-noted and other shortcomings of prior techniques for warning of epileptic seizures.

A preferred form of the invention consists of a sensing portion capable of detecting the onset of a seizure, a signal processing portion, and a therapy delivery portion. The sensing portion may be an electrical sensor, chemical sensor, and/or a sensor for sensing physiological changes. The particular structure and parameter to measure may be selected from any known techniques which provide indication of the possible onset of a seizure. The signal processing portion processes and analyzes the sensed signal using an algorithm for recognizing a pattern scheme indicative of the onset of a seizure. If a pattern indicative of the onset of a seizure is recognized, the therapy delivery portion is triggered. The therapy delivery portion is preferably a stimulation electrode which delivers sensory stimulation to the patient thereby alerting the patient of the onset of a seizure.

Sensory stimulation may encompass any combination of touch, sight or sound stimuli. The patient may then take appropriate action to avoid physical injury. For example, if the patient is driving a car when he/she is given a warning signal under the present invention, the patient may immediately stop the car. Further, research has found that the human body is capable of aborting seizures through sensory self stimulation. For example, some patients who have a sensors experience associated with a partial seizure, called an aura, will slap themselves to prevent the generalized seizure that normally follows. Accordingly, under the present invention, if a patient is provided sensory stimulation warning the patient of the possibility of a seizure onset, the patient may take similar action to prevent the seizure. In fact, if the sensory stimulation is sufficiently intense. it may obviate the need for the patient to do anything since the sensory stimulation is equivalent to slapping themselves. Moreover, the cognitive recognition of the possibility of a seizure may in itself serve to abort the occurrence of the seizure. For example, the patient may engage in a mental activity such as performing mathematical computations to "de-synchronize" the neurons, thereby reducing the hyper-synchronous of the neurons.

Under another embodiment, the invention includes a sensing portion, a signal generating portion and a therapy delivery portion. Under this embodiment, the sensing portion monitors electrical, chemical and/or physiological activity of the patient. The signal generating portion transduces the sensed activity of the patient to a corresponding electrical signal. The therapy delivery portion provides sensory stimulation to the patient based on the electrical signal provided by the signal generating portion. Sensory stimulation may be provided by stimulation of the dorsal column of the spinal cord. Alternatively it may be provided by stimulation of a region of the thalamus or cortex representing a sensory function such as skin sensation or sound, visual or olfactory perception. The patient is thereby provided continuous sensory stimulus relating to electrical, chemical and/or physiological activity of the patient sensed by the sensing portion. Before the patient experiences a seizure, the patient will have sensed a certain pattern of sensory stimulus. After one or more of such seizure episodes, the patient may thereby learn to recognize patterns which are indicative of a seizure onset. By recognizing these patterns, the patient may thereby take appropriate action as discussed herein.

By using the foregoing techniques, seizure disorders, including epilepsy, can be treated and seizures can be alleviated or prevented using sensory stimulation to consciously alert the patient of the onset of a seizure. By alerting the patient of a possible seizure onset, the patient may take action to minimize the risk of injury result from a loss of bodily control. Moreover, mental awareness by the patient of the possibility of a seizure in itself may thereby prevent the seizure from occurring.

Examples of the more important features of this invention have been broadly outlined above in order that the detailed description that follows may be better understood and so that contributions which this invention provides to the art may be better appreciated. There are, of course, additional features of the invention which will be described herein and which will be included within the subject matter of the claims appended hereto.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

The present invention discloses techniques for providing sensory stimulation as a means for desynchronizing the electrical activity of the brain which leads to a seizure. As preferred, the invention includes generally a sensor portion for monitoring the onset of a seizure, a signal processing portion for processing the sensed signals to recognize a pattern indicative of a seizure onset, and a therapy delivery portion for providing sensory stimulation to alert the patient of the possible onset of a seizure.

Figure 1:
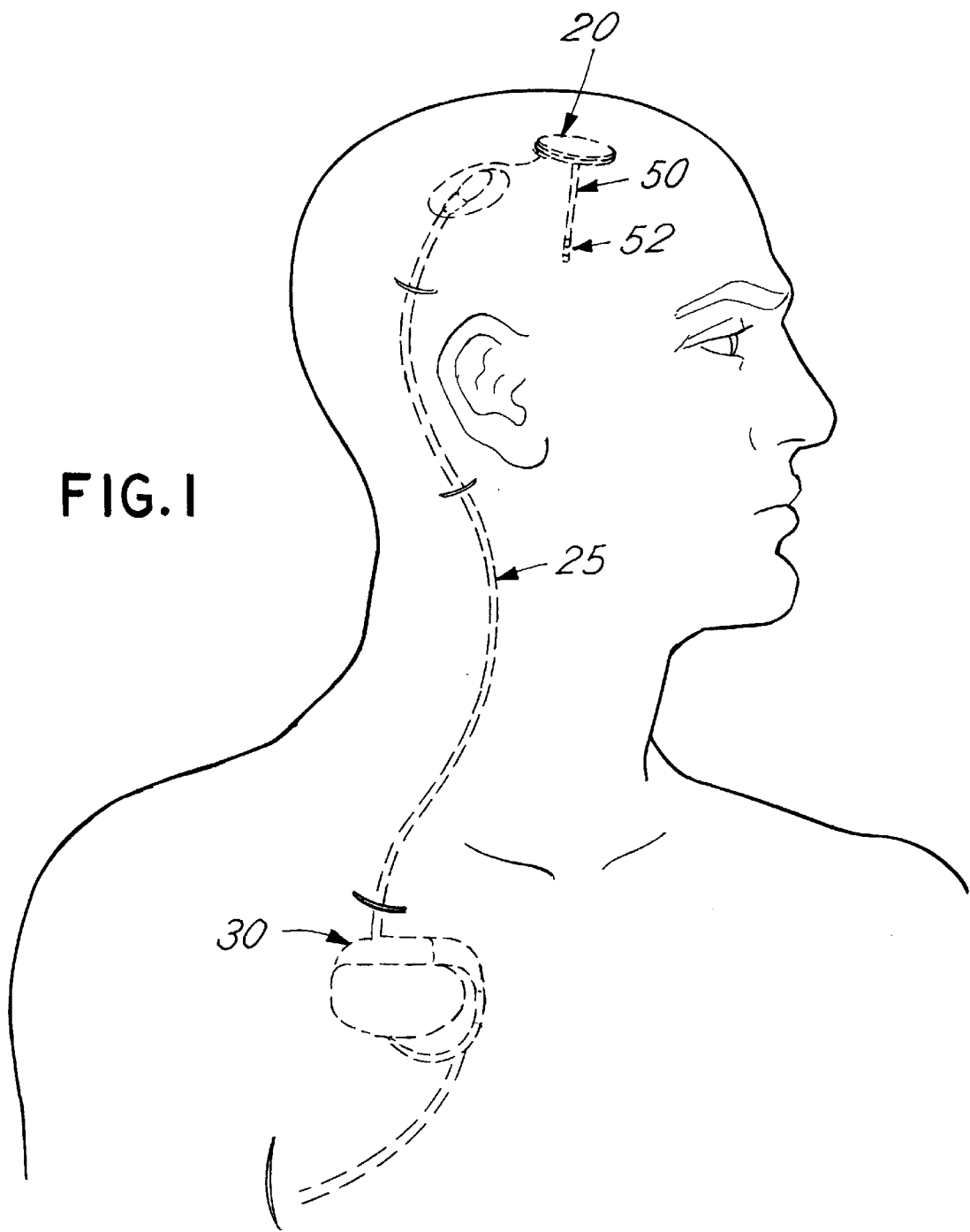
FIG. 1 is a diagrammatic illustration of a preferred embodiment of the present invention having a sensor implanted in a brain, a signal generator and stimulation electrodes.
Figure 2:
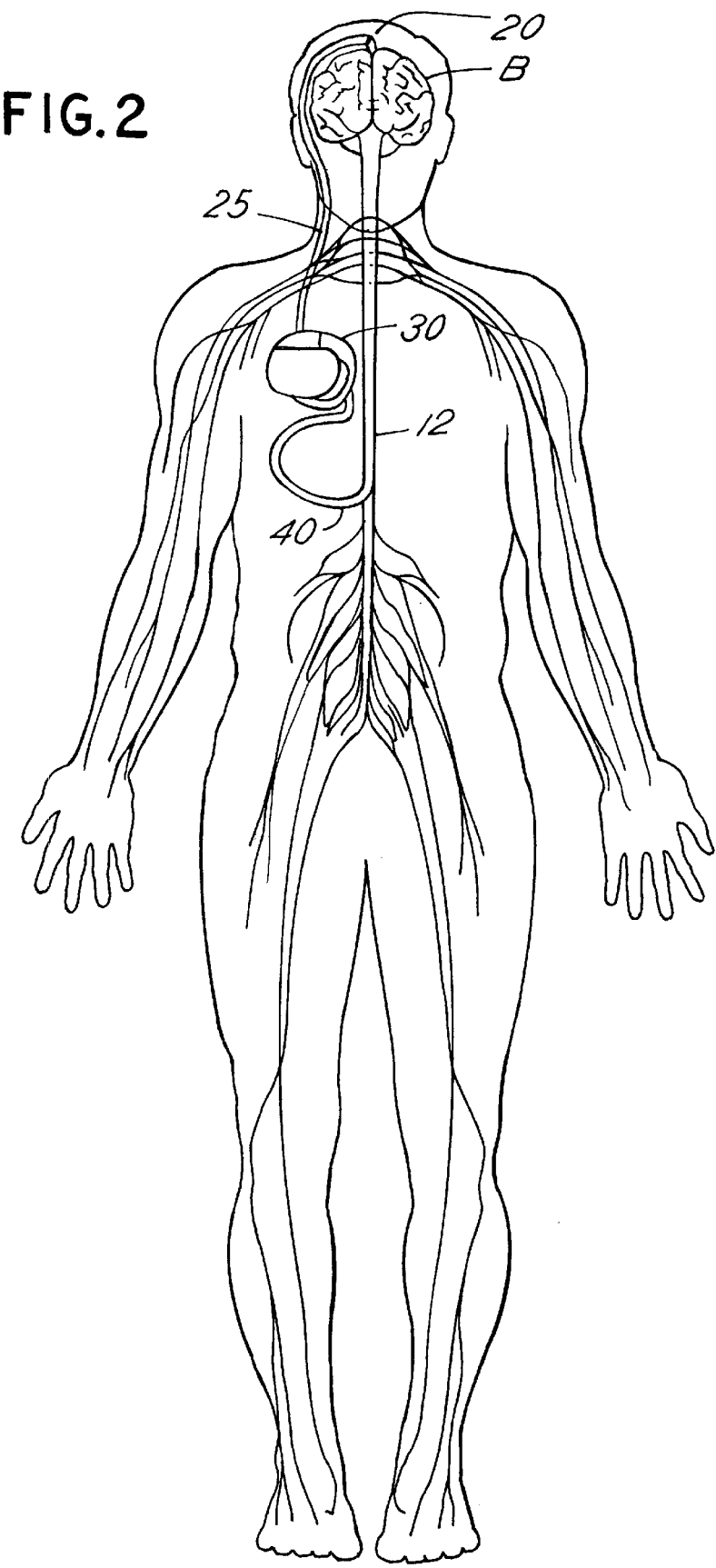
FIG. 2 is a diagrammatic illustration of the embodiment of FIG. 1 depicting the placement of the stimulation electrodes to stimulate a predetermined site of the spinal cord.

Referring to FIGS. 1 and 2, a system made in accordance with the preferred embodiment may be implanted below the skin of a patient. The system includes generally a sensor 20, a signal processor/generator 30 and one or more stimulation electrodes 40.

Sensor 20 serves as the sensing portion of the present invention. Sensor 20 is implanted into a portion of a patient's body suitable for detecting a condition resulting from the onset of a seizure, including a seizure itself. Sensor 20 is adapted to sense an attribute of the body that changes in advance of or during a seizure. Sensor 20 is operatively coupled to provided sensed signals to the signal processor/generator 30. As shown, sensor is coupled via lead 25 to signal processor/generator 30. Alternatively, telemetry may be used to couple components 20 and 30. Signals that are received by the sensor may by amplified before transmission to signal processor/generator 30.

Sensor 20 may take the form of a device capable of detecting nerve cell or axon activity that is related to the pathways at the cause of a seizure symptom, or that indicate sensations which are elicited by the onset of a seizure. As preferred, sensor 20 is located deep in the brain parachyma in appropriate locations as shown in FIG. 1 and consists of a tube 50 implanted into brain B that carries one or more depth wire electrodes near end 52 of tube 50. For such detecting, the electrodes may be inserted into the thalamus, internal capsule, hippocampus, cortex or basal ganglia of brain B. Alternatively, the electrodes may be inserted into the seizure focus or part of the central nervous system where seizures begin.

In other embodiments, sensor 20 may include electrical transducers including subcutaneous electrodes placed on the surface of the skull over appropriate brain structures, peg electrodes implanted into the skull over these brain structures, epidural electrodes, or subdural electrodes placed on the cortical surface of appropriate brain structures. Under these embodiments, brain EEG/ECOG recorded above the cortical surface also may be detected by such a sensor. Sensors placed above the cortical surface may be generally located at two or more locations identified in the International 10-20 system of standard sites for EEG (*Spehlmann's EEG Primer, Second Edition*, Bruce J. Fisch, Elsevier Sciences Publisher BV, 1991).

Alternatively, sensor 20 may be a chemical sensor implanted in the brain B or ventricular space for detecting certain chemical substances such as transmitter substances or the break down products of transmitter substances. Under this alternative, sensor 20 may take the form of a transducer consisting of an electrode with an ion selective coating applied which is capable of directly transducing the amount of a particular transmitter substance or its breakdown by-products found in the interstitial space of a region of the brain B such as the hippocampus or thalamus. The level of the interstitial transmitter substance is an indicator of the relative activity of the brain region and the onset of a seizure. An example of this type of transducer is described in the paper "Multichannel semiconductor-based electrodes for in vivo electrochemical and electro-physiological studies in rat CNS" by Craig G. van Horne, Spencer Bement, Barry J. Hoffer, and Greg A. Gerhardt, published in *Neuroscience Letters*, 120 (1990) 249–252.

As yet another alternative, sensor 20 may sense physiological changes which are indicative of a seizure onset. For example, sensor 20 may transduce physiological changes in the heart rate or respiration. Under this alternative, sensor 20 may be placed near nerve cells controlling muscles and include a device capable of detecting nerve compound action potentials (e.g., either sensory afferent information from muscle or skin receptors or efferent motor potentials controlling a muscle of interest). Alternatively, sensor 20 may detect muscle EMG in one, two or more muscles. Monitored muscles may include the heart, respiratory muscles or reciprocal muscles at one joint. For such detection, sensor 20 may take the form of a lead with one or more recording electrodes inserted into the muscle of interest. In yet other embodiments, sensor 20 may sense heart rate or respiration rate. Sensor 20 may be physically located outside of the body and communicate with the implanted portion through telemetry.

The output of sensor 20 is coupled by cable 25, comprising one or more conductors, to the signal processing portion of the present invention. Alternatively, the output of an external sensor would communicate with the implanted pulse generator through a telemetry downlink. Such telemetric systems may use, for example, radio frequency, ultrasound, infrared or other like communication means.

Figure 3:
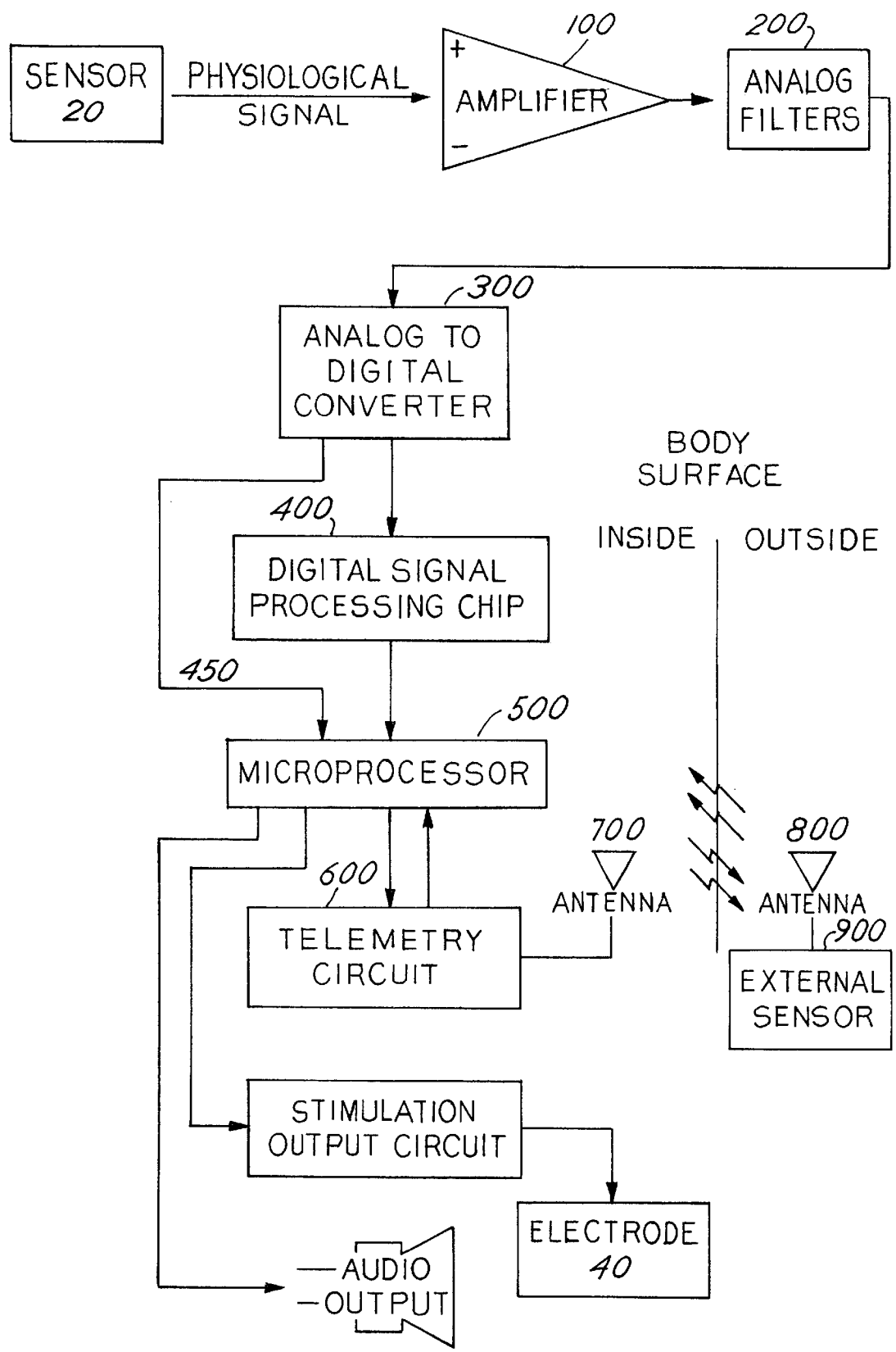
FIG. 3 is a block diagram of the signal processing portion of the present invention.

The signal processing portion of the present invention is preferably included within signal processor/generator 30. Alternatively, signal processor/generator 30 may be separated into a signal processing component and a signal generating component. The signal processing portion or component provides a means for signal processing and means for pattern recognition. FIG. 3 is a block diagram depicting the signal processing portion of the present invention. A signal received from sensor 20 may be processed by amplifying and filtering the signal by amplifier 100 and filter 200 respectively. The signal is then converted to a digital representation by analog to digital converter 300. The signal may then be further processed by a digital signal processing chip 400 or may be input to a microprocessor 500. Microprocessor processes the sensor data in different ways depending on the type of parameter that is sensed by sensor 20. Microprocessor 500 processes the sensor signal and determines whether there exists a threat of a seizure. In particular, microprocessor 500 serves as the means for feature extraction and for pattern recognition. Alternatively, digital signal processing chip 400 could be used to extract features prior to processing by the software algorithm of microprocessor 500. Feature extraction and pattern recognition involves implementing an algorithm to detect the onset of a seizure.

In a preferred embodiment, the software algorithm is performed as follows. Sixteen channels of EEG waves are recorded. These EEG waves are then low-pass filtered at 70 cycles/sec with a 4-pole analog filter and then sampled at 200 samples/sec/channel. The resulting signal is then broken down into simple features by reducing the sinusoidal EEG signal into a sequences of segments. A segment is a section between two consecutive extremes of amplitude and is characterized by duration, amplitude and direction (i.e., slope of the line). A sequence of segments is created to eliminate small amplitude "noise" (beta frequency EEG, muscle artifact). This noise creates smaller intervening segments that face an opposite direction to that of the neighboring larger segments. The sequence combines one or more segments which are faced in the same direction and smaller intervening segments. A sequence ends when a segment not belonging to that sequence is produced. A segment does not belong to a sequence when its direction is opposite to the previous segment and its length is greater than the length of the previous segment. When a sequence is complete, the following operations take place sequentially to determine whether a possible EEG spike or sharp wave (SSW) is detected. First, the relative amplitude of the current sequence and of the preceding one is checked to determine whether they are above a certain threshold. The relative amplitude is the amplitude of the sequence relative to the average amplitudes of the sequences 5 seconds prior to the instant sequence. The relative amplitude is the ratio of the amplitude of the instant sequence to the average amplitude of the previous sequences taken 5 seconds prior. If the relative amplitude is above 4, then the sequence is marked as being part of a SSW. Next, the pseudo-duration of the segment is checked. The pseudo-duration is graphically determined by extending a line from the start of a sequence (point A) through the half-way point of the actual EEG wave and extending it so its end (point B) equals the amplitude level of the ending point of the sequence. The horizontal distance from A to B is the pseudo-duration The sequence is marked as a possible SSW if the pseudo-duration in combination with the relative amplitude reaches above a certain amount. Generally, the shorter the pseudo-duration, the lower the relative amplitude needs to be for a SSW marking. Next, the relative amplitudes are checked in relation to the relative sharpness of the waves. The relative sharpness of the wave is the second derivative of a wave at 15 msec before and after the apex of a wave. The higher the relative sharpness, the lower the relative amplitude required to mark the sequence as a possible SSW. Finally, the total duration of the wave is checked. If it is larger or equal to 35 msec, the sequence is marked as a possible SSW.

Once a sequence or a wave is marked as a possible SSW, further processing is required to possibly reject this wave. For example, the wave is rejected if it is the result of muscle activity, eye blinks or alpha activity. Muscle activity may cause a large number of high amplitude segments in the immediate surrounding of the wave (⅓ sec). Eye blinks may cause SSW marking from an EEG in the frontal channel having positive polarity, has a duration larger than 150 msec, and a wave of similar amplitude occurs simultaneously on the homologous contralateral channel. Alpha activity causes a dominant frequency of 8–12 cycles/sec.

Once a wave is determined to be a SSW, its relationships with other channels are important for localization of an epileptic focus. The above analysis proceeds by discrete time units of about ⅓ sec. If several SSWs are found in a given channel during a time unit, only the sharpest is retained. If SSWs are found in one or more channels within the time unit, an event is said to have occurred. The events from the 16 EEG channels may then be tabulated. Based on the location and occurrence frequency of these events, electrical activity indicating a seizure pattern may be determined. Such a system may be that disclosed by J. Gotman and P. Gloor in *Automatic Recognition and Quantification of Interictal Epileptic Activity in the Human Scalp EEG*. Electroencephalography and Clinical Neurophysiology, 41: 513–529, 1976. The rhythmicity of the electrical activity could also be used to indicate the occurrence of a seizure. The time interval associated with two successive segments is proportional to the frequency of EEG activity. Frequency of EEG activity between 3 to 20 cycles/sec sustained for a sufficient duration indicated the occurrence of a seizure. For example, once a patient suffers a seizure attack, a template may be created which can be used to detect future seizures exhibiting similar EEG activity. Such a template would be patient specific.

Other examples of algorithms to detect the onset of seizures have been reported in U.S. Pat. Nos. 5,311,876 (issue May 17, 1994) and U.S. Pat. No. 5,349,962 (issued Sep. 27, 1994) and by Jean Gotman in *Epilepsy Surgery*, ch. 36 (ed. Hans, Luders, Raven Press, New York 1991) and by Jean Osorio & Mark Frei in Abstracts of the American Epilepsy Society meeting, 1995. These references are incorporated herein by reference. Those skilled in the art will appreciate that any member of other algorithms may be used. An external electronic device may be implemented to telemeter parameter changes or newer algorithms to the implanted signal processing device to adapt the detection algorithm to the particular patient.

Microprocessor 500 is coupled to signal processor/generator 30 and cues the signal processor/generator 30 to generate a signal when a pattern indicative of a seizure is identified. Signal processor/generator 30 is implanted in a human body in a subclavicular, subcutaneous pocket. Alternatively, the signal processor/generator 30 may be implanted elsewhere, such as in the abdomen. Signal processor/generator 30 may take the form of a modified signal generator Model 7424 manufactured by Medtronic, Inc. under the trademark Itrel II which is incorporated by reference. Signal processor/generator 30 may include a frequency generator, a digital to analog converter, and a pulse width control module to vary the type of stimulation to provide as a warning. The stimulus pulse frequency is controlled by programming a value to the programmable frequency generator (not shown). The progammable frequency generator provides an interrupt signal to signal processor/generator 30 when each stimulus pulse is to be generated. The frequency generator may be implemented by model CDP1878 sold by Harris Corporation.

At the time the present invention is implanted within the patient, the clinician programs certain key parameters into the memory of the implanted device or may do so via telemetry. These parameters may be updated subsequently as needed. Alternatively, the clinician may elect to use default values. The clinician must program the range of values for pulse width, amplitude and frequency which microprocessor 500 may use to optimize the therapy. Stimulus parameters can be adjusted (via telemetry) by a computer algorithm within a range specified by the clinician in an attempt to optimize the seizure suppression.

Figure 4:
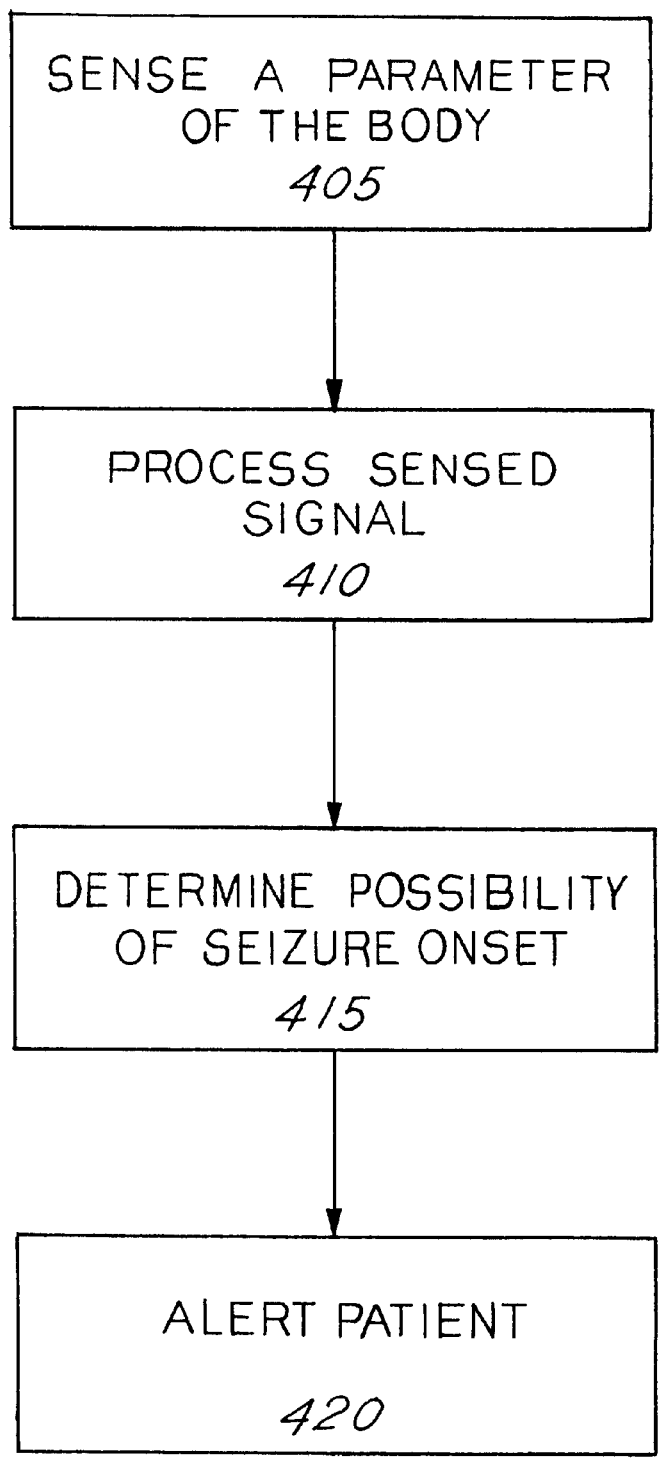
FIG. 4 is a flow chart depicting the steps for alerting the patient of a possible seizure.

FIG. 4 discloses a flow chart for providing a patient with a seizure in accordance with the present invention. At step 405, sensor 20 senses a parameter of the body and generates a signal. At step 410, the signal is processed and, at 415, an algorithm determines whether the sensed signal indicates that there exists a risk of a seizure onset. This step is continually performed. If it is determined that a seizure onset is possible, at step 420, electrodes 40 provide electrical stimulation to provide some sort of sensory stimulus to alert the patient. Alternatively, the sensory stimulus may be strong enough such that it in itself may abort the onset of a seizure.

Simulation electrodes 40 serve as the therapy delivery portion of the present invention. Each electrode 40 is individually connected to the signal processor/generator 30 through a wire conductor. Depending upon the stimulus desired, any number of electrodes may be used. Model 3387 DBS™ electrodes sold by Medtronic, Inc. of Minneapolis, Minn. may be used. Stimulation electrodes 40 serve to produce a sensory experience for the patient based on the signal provided by the signal processor/generator 30. Under the embodiment of FIG. 1, the stimulation electrodes 40 are placed along the spinal cord in the epidural space. The exact placement of the electrodes 40 is dependent upon the type of sensory experience desired. Sensors may be placed to automatically elicit a visual, aural or touch stimulus. An alternative sound stimulus may be an speaker mechanism as found in synchromed pumps. For example, Synchromed® model 8616 pump sold by Medtronic, Inc. may be used. Alternatively, sound may be generated via a piezoelectric sound generator. Alternatively, any combination of touch stimulus, sight stimulus and sound stimulus may be utilized.

In another application, a large sensory stimulus may be desired where the sensory stimulus in itself would serve to prevent the onset of a seizure. In such a case, electrodes 40 may be placed along the anterolateral aspect of the spinal cord to activate the pain fibers of the spinothalamic tract thereby creating a more painful experience. Alternative placement of electrodes 40 may include the dorsal column of the spinal cord, the antero lateral column of the spinal cord, skin nerves, the auditory cortex, the somatosensory cortex, nuclei of sensory thalamus, or the visual cortex.

Yet another arrangement is placement of the electrodes 40 over the somatosensory cortex either by using peg electrodes in the skull (to sense EEG) or epidural electrodes slipped under the skull through a burr hole to stimulate the cortex. Still another option is use of a steerable electrode to allow changes to the desired sensory stimulus. Such an electrode is disclosed U.S. patent application Ser. No. 08/637,361 filed Apr. 25, 1996 and entitled "Techniques for Adjusting the Locus of Excitation of Neural Tissue in the Spinal Cord or Brain." As another embodiment, electrodes 40 may be placed directly under the skin to produce skin senses.

In accordance with another embodiment of the present invention, the system includes generally a sensing portion, a signal generating portion and a therapy delivery portion. Under this embodiment, the sensing portion monitors electrical, chemical and/or physiological activity of the patient. The signal generating portion transduces the sensed activity of the patient to a corresponding electrical signal used to activate a pattern of sensation in one part of the sensory nervous system. The signal generating portion includes generally a signal generator. Under this embodiment, means for pattern recognition, such as algorithms, would not be required. The sensed signal is processed and the therapy delivery portion provides continuous sensory stimulation to the patient representative of the sensed electrical, chemical and/or physiological activity. Alternatively, the patient may receive sensory stimulus in intervals of short time periods. For example intervals of 1–10 seconds may be utilized. Rather than provide the patient with sensory stimulation only when a possible seizure onset is calculated, the patient is provided continuous stimulation. The sensory stimulation provided includes features which are in some way related to the features extracted from the EEG/ECoG containing the most power. The stimulus intensity which is determined by the pulse width and amplitude of the stimulus pulses might be related to the amplitude of the EEG/ECoG. Alternatively, stimulus amplitude might be related to a measure of complexity as described by K. Lehnertz and C. E. Elger ("Neuronal complexity loss in temporal lobe epilepsy: effects of carbamazepine on the dynamics of the epileptogenic focus.", *Electroencephalography and clinical Neurophysiology*, 103 (1997) 376–380. Over time and after one or more seizure episodes, the patient will learn to recognize the stimulation patterns which are indicative of a seizure onset. The human brain which has an inborn ability to recognize patterns may thereby learn to recognize the patterns for the occurrence of seizures.

By using the foregoing techniques for electrical stimulation, seizure patients may be provided adequate warning of a possible seizure onset to avoid the risk of physical injury. The patient may also take action to avoid the possible onset of the seizure. Those skilled in that art will recognize that the preferred embodiments may be altered or amended without departing from the true spirit and scope of the invention, as defined in the accompanying claims.

I claim:

1. A method of warning a patient of a possible onset of a seizure using a sensor, a signal generator and at least one implantable electrode having a proximal end and a stimulation portion, the method comprising the steps of:
    a. surgically implanting the sensor within a body of a patient;
    b. coupling the sensor to the signal generator;
    c. surgically implanting the electrode in the body, coupling the proximal end to the signal generator, and positioning the stimulation portion to be in communication with neural tissue within the body; and
    d. sensing a parameter of the body with the sensor and generating a sensing signal;
    e. detecting from the sensor signal a pattern indicative of the onset of a seizure; and
    f. in response to a detected possible seizure onset, stimulating the neural tissue with the electrode to generate a sensory stimulus to the body.

2. The method of claim 1, wherein the step of surgically implanting the sensor includes the step of positioning the sensor to be in communication with a predetermined site in a brain.

3. The method of claim 2, wherein the step of positioning includes the step of selecting the predetermined site from the group consisting of the thalamus, internal capsule, hippocampus, cortex and basal ganglia.

4. The method of claim 1, wherein the step of sensing includes the step of sensing electrical activity of a brain.

5. The method of claim 1, wherein the step of sensing includes the step of sensing chemical activity of a brain.

6. The method of claim 1, wherein the step of surgically implanting includes the step of surgically implanting the signal generator.

7. The method of claim 6, wherein the step of surgically implanting the signal generator includes the step of placing the signal generator in a subclavicular, subcutaneous pocket of the body.

8. The method of claim 6, wherein the step of surgically implanting the signal generator includes the step of placing the signal generator in an abdomen of the body.

9. The method of claim 1, wherein the step of detecting includes the step of performing an algorithmic operation.

10. The method of claim 9, further comprising the step of changing the algorithmic operation to a second algorithmic operation.

11. The method of claim 1 wherein the step of stimulating includes the step of providing a type of stimulus selected from the group consisting of touch stimulus, visual stimulus, and aural stimulus.

12. The method of claim 1 wherein the step of surgically implanting the electrode includes the step of positioning the electrode to be in communication with a predetermined part of a spinal cord of the body.

13. The method of claim 12, wherein the step of positioning includes the step of selecting the predetermined part from the group consisting of an epidural space, dorsal aspect, anterolateral aspect, and spinothalamic tract.

14. The method of claim 1 wherein the step of surgically implanting the electrode includes the step of positioning the electrode to be in communication with a somatosensory cortex of the brain.

15. The method of claim 1 wherein the step of surgically implanting the electrode includes the step of positioning the electrode to be in communication neural tissue underneath skin tissue of the body.

16. An apparatus for warning a patient of a possible onset of a seizure comprising:
    a. a sensor capable of generating a sensing signal;
    b. a signal processor coupled to receive the sensing signal, to process the signal, and to detect a pattern indicating the possible onset of a seizure,
    a signal generator for generating a stimulation signal in response to an indication by the signal processor; and
    d. at least one electrode having a proximal end and a stimulation portion, the proximal end being coupled to receive the stimulation signal, the stimulation portion coupled to stimulate neural tissue to deliver a sensory stimulus to the body.

17. The apparatus of claim 16, wherein the sensor comprises at least one sensing electrode.

18. The apparatus of claim 17, wherein the sensing electrode is selected from the group consisting of a peg electrode, epidural electrode, subdural electrode, and a subcutaneous electrode.

19. The apparatus of claim 16, wherein the implantable sensor includes a transducer and a sensing electrode having an ion selective coating.

20. The apparatus of claim 16, wherein the sensor has means for sensing physiological changes of a body.

21. The apparatus of claim 16, wherein the signal processor comprises an analog to digital converter, an amplifier and a filter.

22. The apparatus of claim 16, wherein the signal processor includes a microprocessor.

23. The apparatus of claim 16, wherein the sensor is an external device and is capable of telemetrically communicating with the signal processor.

24. The apparatus of claim 16, wherein the signal generator comprises a frequency generator, a digital to analog converter, and a pulse width control module.

25. The apparatus of claim 16, wherein the electrode comprises a steerable electrode.

26. The apparatus of claim 16, wherein the signal generator and signal processor are implantable devices.

27. The apparatus of claim 16, wherein the sensor is an implantable device.

28. A method of warning a patient of a possible onset of a seizure using a sensor, a signal generator and at least one implantable electrode having a proximal end and a stimulation portion, the method comprising the steps of:
   a. implanting the electrode in a body of a patient, coupling the proximal end to the signal generator, and positioning the stimulation portion to be in communication with neural tissue within the body;
   b. positioning a sensor to sense a characteristic of the body;
   c. sensing a parameter of the body and generating a sensing signal;
   d. providing the sensing signal to the signal generator to generate a therapy signal based on the sensing signal; and
   e. periodically stimulating the neural tissue to generate a sensory stimulus based on the therapy signal.

29. The method of claim 28, wherein the step of positioning includes the step of selecting the predetermined site from the group consisting of the thalamus, internal capsule, hippocampus, cortex and basal ganglia.

30. The method of claim 28, wherein the step of sensing includes the step of sensing electrical activity of a brain.

31. The method of claim 28, wherein the step of sensing includes the step of sensing chemical activity of a brain.

32. The method of claim 28, wherein the step of surgically implanting includes the step of surgically implanting the signal generator.

33. The method of claim 32, wherein the step of surgically implanting the signal generator includes the step of placing the signal generator in a subclavicular, subcutaneous pocket of the body.

34. The method of claim 32, wherein the step of surgically implanting the signal generator includes the step of placing the signal generator in an abdomen of the body.

35. The method of claim 28, wherein the step of detecting includes the step of performing an is algorithmic operation.

36. The method of claim 35, further comprising the step of changing the algorithmic operation to a second algorithmic operation.

37. The method of claim 28 wherein the step of stimulating includes the step of providing a type of stimulus selected from the group consisting of touch stimulus, visual stimulus, and aural stimulus.

38. The method of claim 28 wherein the step of surgically implanting the electrode includes the step of positioning the electrode to be in communication with a predetermined part of a spinal cord of the body.

39. The method of claim 38, wherein the step of positioning includes the step of selecting the predetermined part from the group consisting of an epidural space, dorsal aspect, anterolateral aspect, and spinothalamic tract.

40. The method of claim 28 wherein the step of surgically implanting the electrode includes the step of positioning the electrode to be in communication with a somatosensory cortex of the brain.

41. The method of claim 28 wherein the step of surgically implanting the electrode includes the step of positioning the electrode to be in communication neural tissue underneath skin tissue of the body.

42. The method of preventing the onset of a seizure using a sensor, a signal generator and at least one electrode having a proximal end and a stimulation portion, the method comprising the steps of:
   a. positioning the sensor to sense a condition of a patient's body;
   b. positioning the stimulation portion of the electrode to be in communication with neural tissue of the body
   c. coupling the sensor and the proximal end of electrode to the signal generator; and
   d. sensing a parameter of the body with the sensor and generating a sensing signal;
   e. processing the sensing signal by the signal generator to detect a pattern indicative of a seizure onset; and
   f. if the pattern is recognized, providing a sensory stimulus to the neural tissue with the electrode to responsively initiate desynchronization of neural activity.

43. The method of claim 42, wherein the step of providing sensory stimulus includes the step of stimulating a predetermined portion of the neural tissue, the predetermined portion being selected from the group consisting of a dorsal column of a spinal cord, an antero lateral column of the spinal cord, skin nerves, auditory cortex, somatosensory cortex, nuclei of sensory thalamus, and visual cortex.

44. The method of claim 42, wherein the step of positioning includes the step of selecting the predetermined site from the group consisting of the thalamus, internal capsule, hippocampus, cortex and basal ganglia.

45. The method of claim 42, wherein the step of sensing includes the step of sensing electrical activity of a brain.

46. The method of claim 42, wherein the step of sensing includes the step of sensing chemical activity of a brain.

47. The method of claim 42, further comprises the step of surgically implanting the signal generator.

48. The method of claim 47, wherein the step of surgically implanting the signal generator includes the step of placing the signal generator in a subclavicular, subcutaneous pocket of the body.

49. The method of claim 47, wherein the step of surgically implanting the signal generator includes the step of placing the signal generator in an abdomen of the body.

50. The method of claim 42, wherein the step of detecting includes the step of performing an algorithmic operation.

51. The method of claim 50, further comprising the step of changing the algorithmic operation to a second algorithmic operation.

52. The method of claim 42 wherein the step of stimulating includes the step of providing a type of stimulus selected from the group consisting of touch stimulus, visual stimulus, and aural stimulus.

53. The method of claim 42 wherein the step positioning the stimulation portion of the electrode includes the step of positioning the electrode to be in communication with a predetermined part of a spinal cord of the body.

54. The method of claim 53, wherein the step of positioning includes the step of selecting the predetermined part from the group consisting of an epidural space, dorsal aspect, anterolateral aspect, and spinothalamic tract.

55. The method of claim 42 wherein the step positioning the stimulation portion of the electrode includes the step of positioning the electrode to be in communication with a somatosensory cortex of the brain.

56. The method of claim 42 wherein the step positioning the stimulation portion of the electrode includes the step of positioning the electrode to be in communication neural tissue underneath skin tissue of the body.

* * * * *